United States Patent [19]

Petite et al.

[11] Patent Number: 5,264,551
[45] Date of Patent: Nov. 23, 1993

[54] PROCESS FOR CROSS-LINKING OF COLLAGEN BY DIPHENYLPHOSPHORYLAZIDE THE CROSS-LINKED COLLAGEN OBTAINED THEREBY AND COLLAGEN-BASED BIOMATERIALS THUS CROSS-LINKED

[75] Inventors: Hervé Petite, Bron; Philippe Menasche, Paris; Alain Huc, Ste Foy Les Lyon, all of France

[73] Assignee: Bioetica, Lyons, France

[21] Appl. No.: 768,406

[22] PCT Filed: Apr. 10, 1990

[86] PCT No.: PCT/FR90/00253
§ 371 Date: Oct. 7, 1991
§ 102(e) Date: Oct. 7, 1991

[87] PCT Pub. No.: WO90/12055
PCT Pub. Date: Oct. 18, 1990

[30] Foreign Application Priority Data

Apr. 12, 1990 [FR] France ................ 89 04846

[51] Int. Cl.$^5$ .......................... C08H 1/06; A61L 27/00
[52] U.S. Cl. ........................................ 530/356; 530/333
[58] Field of Search .................. 530/356, 333; 514/2, 514/21

[56] References Cited

U.S. PATENT DOCUMENTS

| 3,873,509 | 3/1975 | Mequro | 530/333 |
| 4,755,593 | 7/1988 | Laurea | 514/12 |

FOREIGN PATENT DOCUMENTS 2617855  7/1987  France .

*Primary Examiner*—Michael G. Wityshyn
*Assistant Examiner*—P. Lynn Touzeau
*Attorney, Agent, or Firm*—Lowe, Price, LeBlanc & Becker

[57] ABSTRACT

The invention relates to a process of cross-linking collagen. This process is of the type comprising the formation of amide bonds by means of acylazide groups and is characterized in that the collagen is reacted with diphenylphosphorylazide. The process according to the invention makes it possible to simplify the collagen cross-linking process and to adjust the degree of cross-linking at discretion without introducing any cross-linking agent.

18 Claims, 3 Drawing Sheets

PROCESS FOR CROSS-LINKING OF COLLAGEN BY DIPHENYLPHOSPHORYLAZIDE THE CROSS-LINKED COLLAGEN OBTAINED THEREBY AND COLLAGEN-BASED BIOMATERIALS THUS CROSS-LINKED

The present invention essentially relates to a process for cross-linking of collagen by diphenylphosphorylazide, the cross-linked collagen thus obtained as well as the collagen-based biomaterials thus cross-linked.

It is known that collagen constitutes one third of the proteins in the living being. Its low immunogenicity, its effect on cell development and its high mechanical properties make it definitely advantageous as a raw material for biomaterials. However, when it is implanted, it suffers a more or less rapid degradation depending on the form that it takes (solutions, sponges, films or native tissues), on the implantation site and on the animal species. Said collagen degradation is sometimes desirable (healing dressings), sometimes inconvenient, (bioprosthestic valves, vascular prosthese, etc.).

On the other hand, collagen degradation is a normal process which is part of the growth, of the development and of the renewing of the connective tissues. It is also an integral part of the healing process. Said collagen degradation is caused by a certain number of enzymes, particularly the collagenases which are responsible for the initial attack on the native collagen with the neutral pH. They are said to cleave the three peptide chains simultaneously. The cleavage takes place between the GLY-LEU or GLY-ILE residues. However, It is at present admitted that such degradation requires the cooperative effects of a number of enzymes among which the stromelysin, the gelatinases.

The great advantage, when collagen is used as biomaterial, is to be able to modulate the biodegradability of the collagen depending on the proposed use. Said biodegradability can be modulated in at least two ways which consist either in the addition of enzyme inhibitors (such as α-2-macroglobulin or β-1-anticollagenase), or in the introduction of chemical cross-linking bonds between the collagen molecules. This second method is the most widely because being more efficient as regards the resistance to enzyme degradation. The cross-linking bonds may be obtained either by physical methods which have the advantage of not introducing any chemical agent in the tissue, but which have proved to be rather inefficient, or by chemical methods which are efficient but leave traces of cross-linking agent in the tissue. Thus, glutaraldehyde (abbreviated to GTA) is the cross-linking agent most widely used, unfortunately it has the property of polymerizing when in solution. This is how, during cross-linking of the collagen, there is formation of GTA polymers, which, with time, will salt out GTA monomers (which latter are cytotoxic at concentrations higher than 10-25 ppm) into the surrounding tissues, while making the collagen lose part of its biological properties for which it had been chosen.

In order to avoid using glutaraldehyde, the present inventors has already proposed, in document FR-A-8710317, a process for cross-linking of collagen by the introduction of the azide groups on the carboxyl groups of the side chains of collagen. In this document, the cross-linking was performed by esterifying the collagen carboxylic groups, after what the esters were successively converted into hydrazides, and then into acylazides. Finally, the acylazides reacted in basic medium with the amino functions of the side chains of the collagen in order to give peptide-type bonds. Said process, although very innovating, has the disadvantage of taking a long time since the cross-linking of the collagen takes 8 days and is unpractical to use on an industrial scale.

The present inventors have continued their research with a view to simplifying the cross-linking method without introducing a cross-linking agent in the finished material and while obtaining a degree of collagen cross-linking equivalent to that obtained with the process described in document FR-A-8710317.

Thus, it is the object of the present invention to solve the new technical problem consisting in providing a process for cross-linking collagen which is simplified while not introducing a cross-linking agent in the finished product and reaching a degree of cross-linking of the collagen which is equivalent to that obtained with the prior processes, and notably that described in document FR-A-8710317.

Another object of the invention is to solve the aforesaid new technical problem with a considerably reduced cross-linking time.

The present invention has, for the first time, solved said new technical problems in an extremely simple and reproducible manner, with a process whose parameters can be varied at discretion, so as to adjust at discretion, the degree of cross-linking of the collagen as a function of the anticipated uses, and at low costs.

Thus, in a first aspect, the present invention provides a process for cross-linking of collagen, of the type comprising forming amide bonds by means of acylazide groups, characterized in that the collagen is reacted with diphenylphosphorylazide (DPPA).

In an advantageous embodiment of the process according to the invention, the reaction with DPPA takes place in a non-aqueous solvent medium. Preferably, said non-aqueous solvent is constituted by dimethylformamide (DMF).

In an advantageous variant of embodiment, the DPPA concentration is comprised between 0.0125% and 1.50% by volume/volume, and preferably still between 0.25 and 0.7%.

In an advantageous variant embodiment of the process according to the invention, the reaction with DPPA is carried out by incubation at an incubation temperature comprises between about 0° and 10° C., and preferably about 4° C., for an incubation period of between a few hours and about one day, preferably about one day.

In a particularly advantageous characteristic of the process according to the invention, after reacting the collagen with the DPPA, at least one rinsing is carried out to eliminate the DPPA, then the collagen containing the acylazide groups is introduced in a solution of borate buffer.

In an advantageous embodiment of the process according to the invention, the collagen containing the acylazide groups is incubated in the borate buffer, advantageously at a temperature comprised between about 0° and 10° C., and better still about 40° C., for an incubation period of between a few hours and about one day, and preferably about one day.

In an advantageous embodiment, the borate buffer has a pH about equal to 8.9.

In yet another advantageous embodiment of the process according to the invention, the collagen used as starting material and reacted with the DPPA is in the form of gel, film or natural tissue, such as pericardium or vascular graft.

In a second aspect, the present invention also covers the collagen cross-linked by means of diphenylphosphorylazide.

The invention also covers the cross-linked collagen, characterized in that it is obtained by the cross-linking process described hereinabove.

Finally, the invention also covers all the collagen-based biomaterials, characterized in that they have been cross-linked by means of the DPPA.

Without knowing for certain the reactional mechanism which causes the cross-linking of collagen by DPPA, it is possible, by reasoning by analogy with the reaction mechanism proposed for the formation of amide bond by DPPA on carboxylic acids, to propose the reaction mechanism shown in appended FIG. 1. It is observed that the carboxylic anion (a), which is supplied by the lateral carboxylic groups of the aspartic or glutamic acid of the collagen peptide chains, can attack the phosphor atom of the DPPA (b) in order to give essentially a pentacovalent phosphorous compound (c). Then, there occurs a migration of the azide group of the phosphor atom towards the carboxylic carbon atom by a rearrangement of the internal nucleophilic substitution type.

Finally, the acylazide formed (d) is going to react with the lateral amino groups of the lysin and hydrolysin of the peptide chains of collagen in order to give an amide type bond.

It is thus found that the invention makes it possible to simplify the collagen cross-linking process in a totally unexpected way, said process being extremely simple, inexpensive and requiring only a relatively short cross-linking period, this representing a remarkable technical advantage, which, for anyone skilled in the art, is a decisive factor over the prior techniques.

Other aims, characteristics and advantages of the invention will become obvious from the following explanatory description of several examples of embodiments which are given solely by way of illustration and therefore cannot in any way limit the scope of the invention.

EXAMPLE 1

Figure 1:
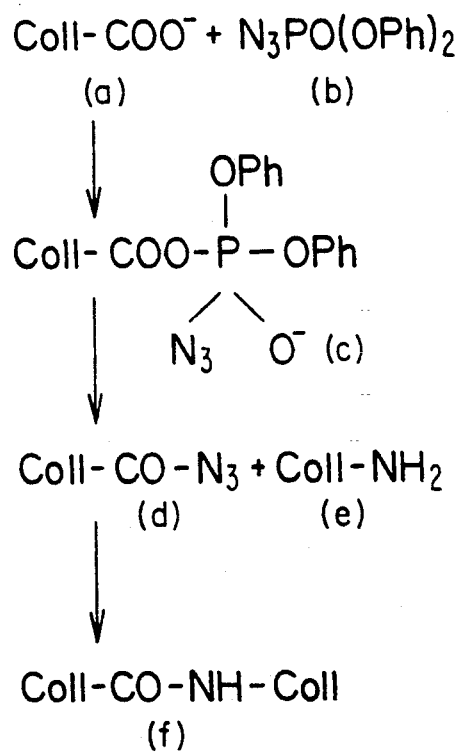
FIG. 1 represents one hypothesis of reaction mechanism of the collagen cross-linking reaction consisting in reacting diphenylphosphorylazide with the carboxylic groups of the collagen.

Cross-linking of calf pericardium with DPPA a) Preparation of the starting material The calf pericardium is collected from the slaughterhouse less than one hour after slaughtering. The fat is removed from the pericardium which is then washed in a solution of NaCl at 0.9%. It is then cut into pellets of 1 cm2, with a punch.

b) Cross-linking of the pericardium:

This reaction can be summed up as follows:

Four pellets of pericardium, previously rinsed in 10 ml of pure DMF for 5 mins. in order to free the tissue from its water, are incubated for 24 jours at 4° C. in 10 ml of a solution of DMF containing 0.75% DPPA (concentration expressed as volume/volume). Then the DPPA is removed from the tissue by rinsing in 10 ml of DMF solution. The DMF is then eliminated by rinsing in 10 ml of a solution of borate buffer with a pH of 8.9 (sodium tetraborate 0.04M, boric acid 0.04M). The tissue is finally incubated for one night in a borate buffer of pH 8.9. Then the tissue is kept, for example, in a solution of ethanol at 70°.

EXAMPLE 2

Cross-linking of a collagen film with DPPA a) Preparation of the starting material.

A gel is prepared from calf skin washed and pared off beforehand with a mixture of lime and sulphide. The skin is then neutralized, then the salts are eliminated by two washes in water. The skin is then ground, and washed with phosphate buffer of pH 7.8 (potassium dihydrogenophosphate 0.78 g/l and disodic monohydrogenophosphate 21.7 g/l). The phosphate is thereafter eliminated by two successive washes with ion-exchanged water. The ground material is then acidified with an acetic acid solution at 10%, the quantity of acetic acid being 5% with respect to collagen. The ground material is then kneaded until a homogeneous paste is obtained. This paste is then diluted to obtain a gel having a collagen concentration of 0.7%. The gel is then placed in small Teflon molds, and allowed to evaporate. The resulting film is thereafter cut with a punch into pellets of 1 cm2.

b) Cross-linking of the film:

This reaction can be summed up as follows:

Four pellets of films of surface 1 cm2 are incubated for 24 hours at 4° in 10 ml of a solution of DMF containing 0.25% of DPPA (concentration expressed in volume/volume). The DPPA is then removed from the film by rinsing with 10 ml of DMF solution. The DMF is then eliminated by rinsing with 10 ml of a borate buffer solution of pH 8.9 (sodium tetraborate 0.04M, boric acid 0.04M). Finally, the films are incubated for one night in a borate buffer of pH 8.9. They are then drained on a filter-paper, and dried in the open. They can afterwards be sterilized, for example with gamma rays.

Sponges, tubes, collagens strands, etc., may be cross-linked in the same way.

EXAMPLE 3

A. Influence of DPPA concentration on the cross-linking of calf pericardium

A first part of the work consisted in studying the influence of DPPA concentration on the degree of cross-linking of the pericardium. To this effect, the pericardium is incubated in DPPA solutions at concentrations varying between 0.0125% and 1.5% (volume/volume).

The degree of cross-linking of the collagen is measured by scanning calorimetric analysis. This technique consists in measuring, during a linear rise in temperature, the difference of energy to be supplied to the sample and to a reference in order to keep them at an identical temperature. When the collagen is denatured, a heat absorption peak appears on the recorder. The beginning of denaturation temperature (TD), the peak of denaturation temperature (TP) and the end of denaturation temperature (TF) are defined in this way.

The following calculation is made in order to calculate a collagen cross-linking percentage R:

$$R = \frac{(TX - TI)}{(TM - TI)} \times 100$$

TM: maximum denaturation temperature which it is possible to obtain when cross-linking collagen with DPPA; in fact, in the present case, it corresponds to the temperature obtained with an 0.75% DPPA concentration ([DPPA]).

TI: temperature of denaturation obtained on the non-treated tissue.

TX: temperature of denaturation obtained on the tissue with a DPPA concentration X.

Figure 2:
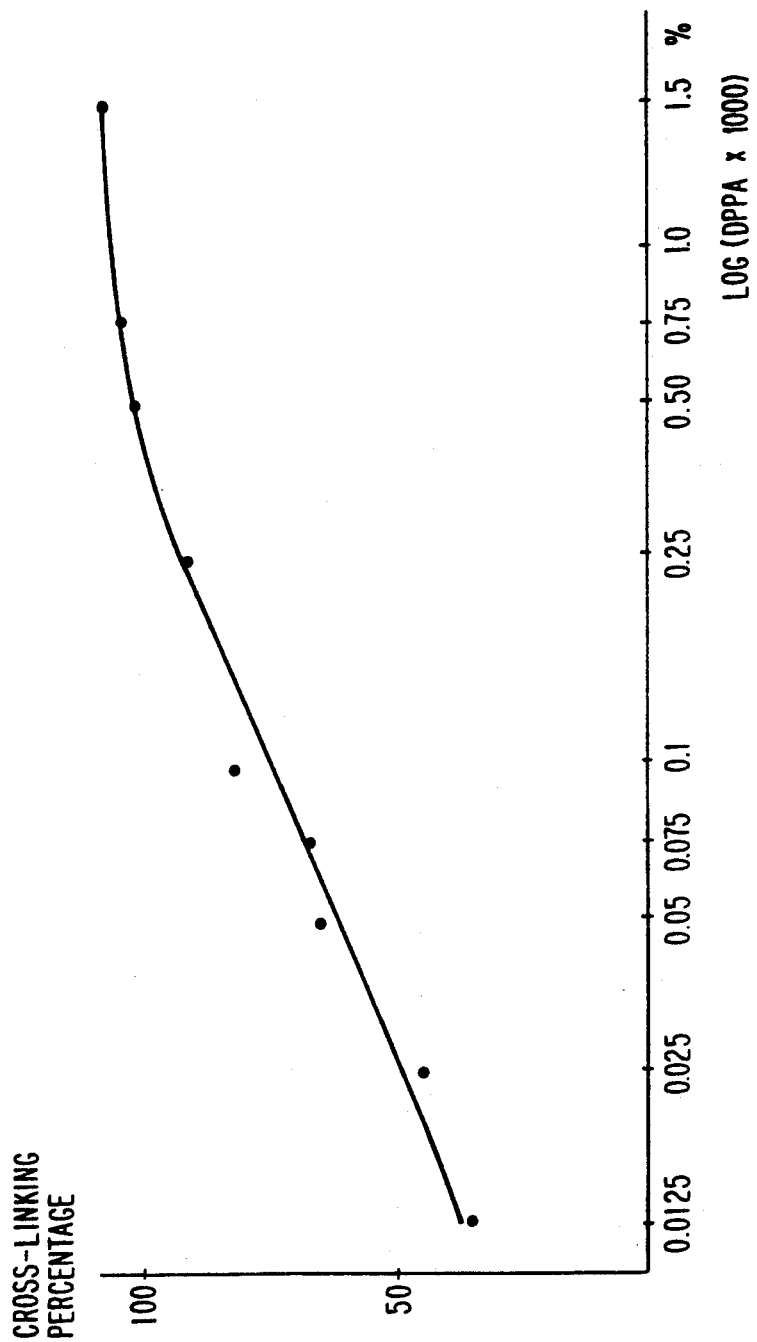
FIG. 2 represents the evolution of the collagen cross-linking percentage, called RTP, measured from the collagen denaturation peak temperature (TP), on calf pericardium as a function of the DPPA concentration.

R is the crosslinking % calculated from TP, the denaturation peak temperature, and is called RTP. The evolution of RTP as a function of the Log([DPPA]×1000) is represented in FIG. 2. The inventors thus determine that between 0.0125% and 0.50% the evolution of RTP as a function of the Log ([DPPA]×1000) is linear and that from 0.5-0.75%, the cross-linking is maximum and constant whatever the DPPA concentration.

When comparing the temperature of denaturation obtained with 0.75% or 0.5% DPPA with that obtained with the process proposed in Patent No. 8710317 and with that of 0.6% GTA (conventional treatment of bioprosthetic values), it is found that these values are not significantly different (Table I).

B. Influence of the DPPA concentration of the cross-linking of collagen film

We have studied the influence of the DPPA concentration on the degree of cross-linking of the collagen film. To this effect, the film is incubated in solutions of DPPA of concentrations varying between 0.0125% and 1.0% (volume/volume).

Figure 3:
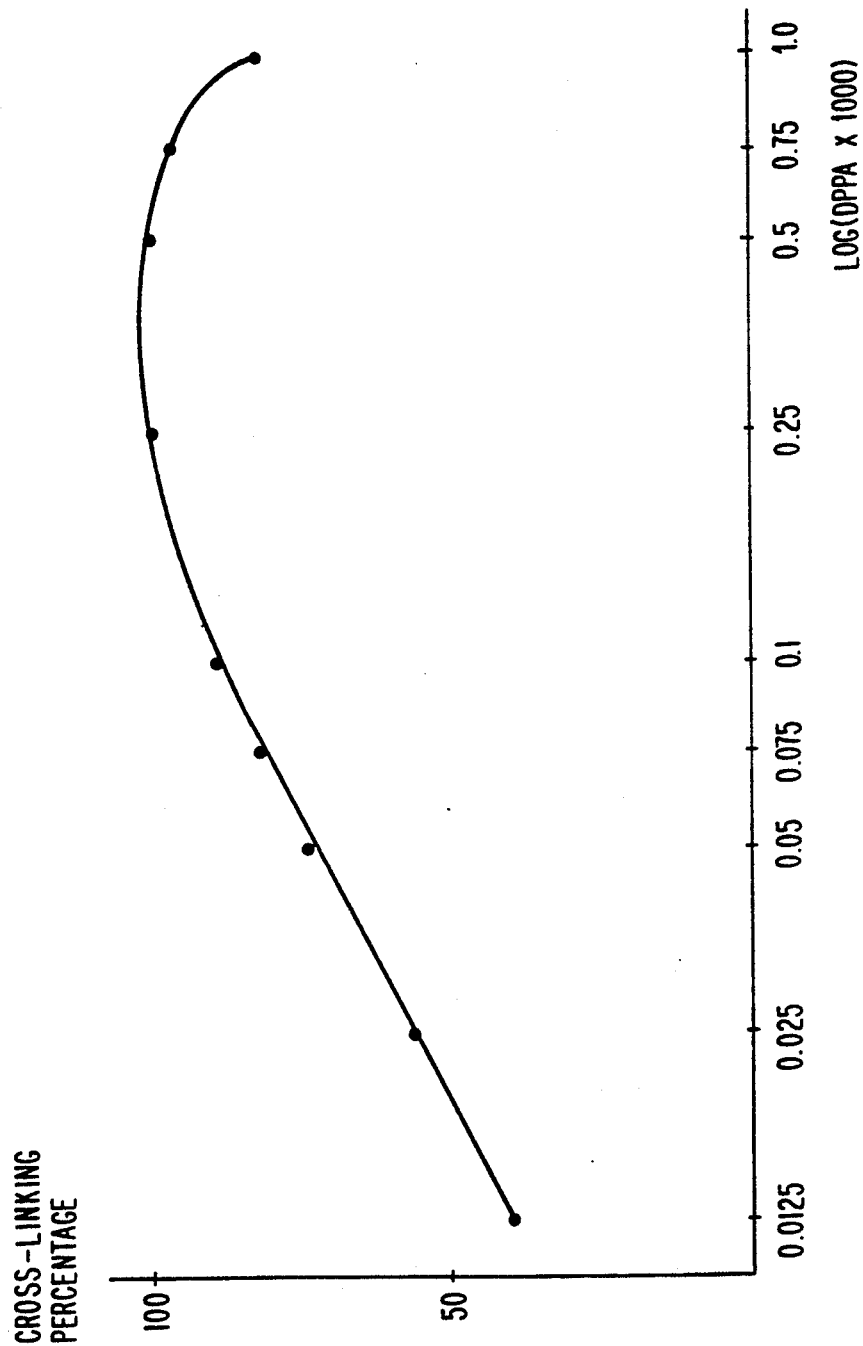
FIG. 3 represents the evolution of the cross-linking RTP percentage on collagen films as a function of the DPPA concentration.

The evolution of the RTP as a function of the Log ([DPPA]×1000) (FIG. 3) is calculated exactly as with the calf pericardium. In this way, the inventors determine that between 0.0125% and 0.10%, the evolution of the RTP as a function of the Log ([DPPA]×1000) is linear. A maximum cross-linking is obtained with DPPA concentrations of 0.25%-0.5%.

When comparing the temperature of denaturation obtained with 0.15% or 0.5% DPPA with that obtained with the process proposed in Patent No. 8710317 and with that of 0.6% GTA (conventional treatment of the bisprosthetic valves), it is found that these values are not significantly different (Table I).

C. DPPA dosage after cross-linking of pericardium

In order to determine what happens to the DPPA after cross-linking, a dosage of the DPPA is effected via its phosphorous group.

Firstly, the phosphorous is dosed on the material treated with the DPPA at different concentrations without any rinsing. The treated material is simply dried in an oven at 110° C. Dosage of the phosphorous is achieved by plasma emission spectrometry after mineralization by a solution of perchloric and nitric acids (two-thirds/one-third in volume/volume). The results are given in phosphorous % with respect to the weight of the dry tissue. The results are recorded in Table II.

Secondly, the phosphorous is dosed on the material treated with the DPPA at concentrations of 0.5% and 1.0% after rinsing the tissue either in borate buffer only, or in DMF and then in borate buffer. The results are recorded in Table III.

TABLE I

Comparison of the temperatures of denaturation of calf pericardium or collagen film treated with GTA, with the acylazides according to the process of Patent No. 8710317, with DPPA, or non-treated.

|  | Temperature of denaturation °C. | | |
|---|---|---|---|
|  | TD | TP | TF |
| Fresh pericardium | 64.30 | 67.30 | 81.30 |
| GTA pericardium 0.6% | 82 | 85.30 | 93.80 |
| Azide pericardium | 78 | 81.40 | 89.10 |
| DPPA pericardium 0.5% | 78.50 | 81.40 | 91.70 |
| DPPA pericardium 0.75% | 79.20 | 82 | 89.90 |
| Non-treated film | 39.15 | 49.12 | 66.10 |
| GTA film 0.6% | 71.10 | 79.10 | 86.40 |
| Azide film | 65.50 | 74.40 | 83 |
| DPPA film 0.25% | 69.90 | 72.70 | 80.50 |
| DPPA film 0.50% | 70.30 | 72.60 | 79.20 |

TABLE II

Percentage of residual phosphorous dosed directly after treatment of the pericardium with DPPA at concentrations ranging between 0% and 1.5%. No rinsing being carried out after treatment with DPPA.

| [DPPA] % | 0.00 | 0.25 | 0.50 | 0.75 | 1.00 | 1.50 |
|---|---|---|---|---|---|---|
| Phosphorous % | 0.1 ± 0.0 | 1.0 ± 0.1 | 1.4 ± 0.2 | 1.7 ± 0.2 | 1.7 ± 0.2 | 2.2 ± 0.1 |

TABLE III

Dosage of residual phosphorous after treatment of the pericardium with DPPA at concentrations of 1.0% to 0.5%. The quantity of phosphorous determined after rinsing the tissue 3 times in borate for a concentration of 0.5% is not different from that determined for a tissue incubated in DMF without any cross-linking agent (see Table II).

| DPPA concentration | No rinses in DMF 3 rinses in borate | 3 rinses in DMF 3 rinses in borate | 5 rinses in DMF 3 rinses in borate | 8 rinses in DMF 3 rinses in borate |
|---|---|---|---|---|
| 1.0% | 0.22 ± 0.02 | 0.23 ± 0.06 | 0.17 ±·0.03 | 0.18 ± 0.01 |
| 0.5% | 0.09 ± 0.06 | 0.04 ± 0.05 | 0.09 ± 0.03 | 0.1 ± 0.06 |

It appears that with a DPPA concentration of 0.5%, the residual phosphorous, even after only three rinses with borate buffer, is equivalent to that noted for a pericardium incubated in DMF without any cross-linking agent (respectively 0.09% and 0.1%).

Thus it appears that the cross-linking agent does not remain in the tissue after cross-linking. Accordingly, this new process seems to be quite an innovation. It allows, just like the process proposed in document FR-A-8710317, cross-linking of the collagen without the permanent introduction of a cross-linking agent and, moreover, its use is made definitely easier at the industrial level.

Naturally, the invention includes all the means constituting technical equivalents of the described means as well as various combinations thereof.

We claim:

1. Process for cross-linking of collagen wherein acylazide groups are used in the formation of amide bonds, characterized in that the collagen is reacted with diphenylphosphorylazide (DPPA).

2. Process according to claim 1, characterized in that the reaction with DPPA takes place in a non-aqueous solvent medium.

3. Process according to claim 2, characterized in that the non-aqueous solvent is dimethylformamide.

4. Process according to claim 1, characterized in that the DPPA concentration is between 0.0125% and 1% in volume/volume.

5. Process according to claim 4, characterized in that the DPPA concentration is between 0.25 and 0.70% in volume/volume.

6. Process according to claim 1, characterized in that the reaction is obtained by incubation at a temperature between about 0 and about 10° C.

7. Process according to claim 6, characterized in that the reaction is obtained by incubation at a temperature of about 4° C.

8. Process according to claim 6, characterized in that the incubation period is between a few hours and about one day.

9. Process according to claim 8, characterized in that the incubation period is about one day.

10. Process according to claim 1, characterized in that after reaction with DPPA, at least one rinse is carried out to eliminate the DPPA, then the collagen containing acylazide groups is introduced into a solution of borate buffer.

11. Process according to claim 10, characterized in that an incubation is effected at a temperature between about 0° and about 10° C. in the borate buffer.

12. Process according to claim 11, wherein the incubation is effected at a temperature of 4° C.

13. Process according to claim 11, characterized in that the borate buffer has a pH of about 8.9.

14. Process according to claim 1, characterized in that the collagen used as starting material is in the form of gel, of film or of tissue graft.

15. Process according to claim 14, wherein the collagen is in the form of pericardium or vascular graft.

16. Cross-linked collagen, characterized in that it is obtained by the process of claim 1.

17. Cross-linked collagen, characterized in that it is cross-linked by means of diphenylphosphorylazide.

18. Collagen-based biomaterial, characterized in that it has been cross-linked by means of diphenylphosphorylazide.

* * * * *

UNITED STATES PATENT AND TRADEMARK OFFICE
CERTIFICATE OF CORRECTION

PATENT NO. : 5,264,551
DATED : November 23, 1993
INVENTOR(S) : Herve PETITE et al.

It is certified that error appears in the above-indentified patent and that said Letters Patent is hereby corrected as shown below:

Title Page:
Please delete section [30] and substitute the following therefor:

--[30]   Foreign Application Priority Data
Apr. 12, 1989 [FR]  France..............89 04846--

Signed and Sealed this

Second Day of August, 1994

Attest:

BRUCE LEHMAN

Attesting Officer         Commissioner of Patents and Trademarks